(12) United States Patent
Choi et al.

(10) Patent No.: US 9,795,574 B2
(45) Date of Patent: Oct. 24, 2017

(54) METHOD FOR PREPARING AGOMELATINE COCRYSTALS AND COMPOSITION CONTAINING SAME

(71) Applicant: SOONCHUNHYANG UNIVERSITY INDUSTRY ACADEMY COOPERATION FOUNDATION, Chungcheongnam-do (KR)

(72) Inventors: Guang Jin Choi, Gyeonggi-do (KR); Min-Jeong Lee, Busan (KR); Nan-Hee Chun, Busan (KR); Keon-Hyoung Song, Chungcheongnam-do (KR)

(73) Assignee: SOONCHUNHYANG UNIVERSITY INDUSTRY ACADEMY COOPERATION FOUNDATION (KR)

( * ) Notice: Subject to any disclaimer, the term of this patent is extended or adjusted under 35 U.S.C. 154(b) by 0 days.

(21) Appl. No.: 15/323,063

(22) PCT Filed: Jun. 30, 2015

(86) PCT No.: PCT/KR2015/006705
§ 371 (c)(1),
(2) Date: Dec. 29, 2016

(87) PCT Pub. No.: WO2016/003161
PCT Pub. Date: Jan. 7, 2016

(65) Prior Publication Data
US 2017/0128391 A1 May 11, 2017

(30) Foreign Application Priority Data

Jun. 30, 2014 (KR) .................. 10-2014-0080808

(51) Int. Cl.
*A61K 31/165* (2006.01)
*C07C 233/18* (2006.01)
*A61K 47/48* (2006.01)

(52) U.S. Cl.
CPC ........ *A61K 31/165* (2013.01); *A61K 47/4803* (2013.01); *C07C 233/18* (2013.01); *C07B 2200/13* (2013.01)

(58) Field of Classification Search
CPC ........................... A61K 31/165; C07C 233/18
See application file for complete search history.

(56) References Cited

U.S. PATENT DOCUMENTS

| | | |
|---|---|---|
| 2012/0316245 A1 | 12/2012 | Letellier et al. |
| 2013/0005820 A1 | 1/2013 | Shan et al. |
| 2014/0011883 A1 | 1/2014 | Huang et al. |
| 2014/0051887 A1 | 2/2014 | Miller et al. |

FOREIGN PATENT DOCUMENTS

| | | |
|---|---|---|
| EP | 2551257 A1 | 1/2013 |
| KR | 10-2014-0008370 A | 4/2007 |
| KR | 10-1404836 B1 | 6/2014 |
| WO | 2012/146371 A1 | 11/2012 |

OTHER PUBLICATIONS

KR1404836, 2014, english machine translation.*
Yan et al.: "Improving the Solubility of Agometatine via Cocrystals"; Crystal Growth & Design, vol. 12 (2012), pp. 2226-2233.
Zheng et al.: "Structures of Polymorphic Agomelatine and Its Cocrystals with Acetic Acid and Ethylene Glycol"; Crystal Growth & Design, vol. 11 (2011), pp. 466-471.
International Search Report for PCT/KR2015/006705, dated Aug. 13, 2015.

* cited by examiner

*Primary Examiner* — Sun Jae Yoo
(74) *Attorney, Agent, or Firm* — Merchant & Gould P.C.

(57) ABSTRACT

The present invention provides a preparation method for agomelatine-resorcinol and agomelatine-hydroquinone co-crystals using the solvent-antisolvent method that enables a commercial mass production. The co-crystals prepared by the preparation method of the present invention displays high dissolution rate and high stability in acidic-to-neutral media.

9 Claims, 8 Drawing Sheets

METHOD FOR PREPARING AGOMELATINE COCRYSTALS AND COMPOSITION CONTAINING SAME

This application is a National Stage Application of PCT/KR2015/006705, filed 30 Jun. 2015, which claims benefit of Korean Patent Application No. 10-2014-0080808, filed 30 Jun. 2014, the contents of all of which are hereby incorporated by reference in their entireties.

TECHNICAL FIELD

The present invention relates to a novel method for preparing agomelatine-resorcinol and agomelatine-hydroquinone co-crystals and a pharmaceutical composition comprising agomelatine-resorcinol and agomelatine-hydroquinone co-crystals.

BACKGROUND ART

Agomelatine is the first antidepressant that acts as an agonist of melatonin MT1 and MT2 receptors and an antagonist of 5-HT2C at the same time. Due to these two properties, agomelatine can be used as a novel antidepressant to recover the severely damaged biologic rhythm of melancholic patients. Agomelatine is a melatonergic antidepressant developed by the pharmaceutical company Servier and commercially available under the trade names of Valdoxan, Melitor, Thymanax, etc. It is marketed for the treatment of major depressive disorders and reported to cause neither withdrawal symptoms nor sexual dysfunction in relation to other antidepressants and to have favorable effects on sleep disorders (insomnia). According to the new clinical results announced in the 31$^{th}$ ECNP (European College of Neuropsychopharmacology) congress, agomelatine is far greater in antidepressant efficacy than the existing classes of antidepressants, SSRI (Selective Serotonin Reuptake Inhibitor) and SNRI (Serotonin Noradrenaline Reuptake Inhibitor).

However, agomelatine with such a great efficacy has too low solubility to display its efficacy. For improving the solubility of agomelatine, many studies have been made on the polymorph forms and co-crystals of agomelatine.

A recent patent application discloses an agomelatine co-crystal using an aromatic polyhydric alcohol to enhance the solubility and dissolution rate (KR Patent Application No. 10-2014-0033531). But, there is still a need for a novel preparation method of preparing agomelatine co-crystals that is designed for the higher process efficiency or easy to apply in the commercial mass production than the conventional preparation methods that are associated with removal of organic solvents and grinding.

PRIOR ART DOCUMENTATION

Patent Documents

Patent Document 1: US 2012-0316245
Patent Document 2: EP 2,551,257
Patent Document 3: KR 2014-0033531

Non-Patent Documents

Non-Patent Document 1: Y. Yan, J-M. Chen, N. Geng, T-B. Lu, Improving the solubility of agomelatine via co-crystals, Crystal Growth and Design, 12 (2012) 2226-2233.

Non-Patent Document 2: S-L. Zheng, J-M. Chen, W-X. Zhang, T-B. Lu, Structures of polymorphic agomelatine and its co-crystals with acetic acid and ethylene glycol, Crystal Growth and Design, 11 (2011) 466-471.

DISCLOSURE OF INVENTION

Technical Problem

It is therefore an object of the present invention to provide a preparation method for agomelatine co-crystals with high yield and purity. The preparation method for agomelatine co-crystals according to the present invention involves a process easy and simple to perform and thus makes it possible to realize a commercial mass production.

It is another object of the present invention to provide a composition comprising agomelatine co-crystals with higher thermal stability and crystallinity as prepared by the above-mentioned preparation method.

Technical Solution

The present invention provides a method for preparing co-crystals of agomelatine and an aromatic polyhydric alcohol according to the solvent-antisolvent method.

The preparation method of the present invention comprises: (i) dissolving agomelatine and the aromatic polyhydric alcohol in an organic solvent selected from the group consisting of C3-C7 ester, C2-C7 ether and a mixture thereof to prepare a solution; and (ii) adding a solvent selected from the group consisting of C5-C7 alkane, benzene and a mixture thereof as an antisolvent to the solution of the step (i) to prepare a mixture.

In the embodiments of the present invention, the aromatic polyhydric alcohol may be benzenediol, preferably hydroquinone, resorcinol, or a mixture thereof.

In the embodiments of the present invention, the co-crystal of the agomelatine and the aromatic polyhydric alcohol may be either an agomelatine-resorcinol co-crystal or an agomelatine-hydroquinone co-crystal.

In the preparation of the co-crystal of the agomelatine and the aromatic polyhydric alcohol according to the present invention, the co-crystal may comprise the agomelatine and the aromatic polyhydric alcohol at a molar ratio of 1:1 to 1:2.

In the preparation of the co-crystal of the agomelatine and the aromatic polyhydric alcohol according to the present invention, the organic solvent may be methylacetate, ethylacetate, diethylether, methyl-tert-butylether, or a mixture thereof.

In the preparation of the co-crystal of the agomelatine and the aromatic polyhydric alcohol according to the present invention, the antisolvent may be pentane, hexane, heptane, benzene, or a mixture thereof.

The present invention also provides a method for preparing an agomelatine-resorcinol co-crystal using the solvent-antisolvent method.

The present invention comprises the steps of: (i) dissolving agomelatine and resorcinol in an organic solvent selected from the group consisting of C3-C7 ester, C2-C7 ether and a mixture thereof to prepare a solution; and (ii) adding a solvent selected from the group consisting of C5-C7 alkane, benzene or a mixture thereof as an antisolvent to the solution of the step (i) to prepare a mixture.

In the preparation method of the present invention, the co-crystal of agomelatine and resorcinol can be produced with higher yield and purity, and the process is so simple as to be applied to a mass production with ease.

The agomelatine-resorcinol co-crystal of the present invention has a powder X-ray diffraction pattern showing peaks (±0.2°) at Bragg angles (2 theta) of 7.25°, 7.95°, 8.35°, 14.45°, 16.70°, 17.35°, 17.95°, 19.05°, 19.95°, 21.30°, 21.75°, 22.50°, 23.75°, and 24.40°.

Further, the agomelatine-resorcinol co-crystal of the present invention has a single endothermic peak in the differential scanning calorimetry (DSC) curve at 88° C. when the heating rate is 10° C./min.

In the preparation method of the present invention, the method may further comprise a step of stirring the mixture of the step (ii). The stirring step may be carried out under the conditions of minimizing the evaporation of the solvent contained in the mixture. For example, the stirring may be performed while the container of the mixture is covered with a lid.

After the addition of the antisolvent, the mixture is stirred to form co-crystals. The mixture containing the co-crystals is subjected to vacuum filtration to yield co-crystals.

In the step (i) of the preparation method for agomelatine-resorcinol co-crystal according to the present invention, the amounts of the agomelatine and resorcinol dissolved in the organic solvent are preferably controlled so that 1 to 2 moles of resorcinol is used per one mole of agomelatine.

In the present invention, the organic solvent may be methylacetate, ethylacetate, diethylether, methyl-tert-butylether, or a mixture thereof, preferably ethylacetate.

In the step (ii) of the preparation method for agomelatine-resorcinol co-crystal according to the present invention, the antisolvent means a solvent having a great difference in solubility parameter from the drug and a conformer used as a solute, that is, having a very low solubility to the solute. In the present invention, the antisolvent may be a solvent that has a lower solubility to a drug than the previously added organic solvent.

Such an antisolvent is primarily used as an accelerating agent for the creation of crystals or co-crystals through the actions of cohesion, precipitation, etc. In the present invention, the antisolvent may be pentane, hexane, heptane, benzene, or a mixture thereof, preferably hexane.

In the present invention, the volume ratio of the organic solvent of the step (i) to the antisolvent of the step (ii) may be 1:1 to 1:3, preferably 1:2.

In the preparation method for agomelatine-resorcinol co-crystal according to the present invention, the stirring speed may be arbitrarily determined by those skilled in the art depending on the reacting dose. The reaction temperature is preferably the room temperature such as 20 to 30° C.

The present invention also provides a method for preparing an agomelatine-hydroquinone co-crystal using the solvent-antisolvent method.

The present invention comprises the steps of: (i) dissolving agomelatine and hydroquinone in an organic solvent selected from the group consisting of C3-C7 ester, C2-C7 ether and a mixture thereof to prepare a solution; and (ii) adding a solvent selected from the group consisting of C5-C7 alkane, benzene or a mixture thereof as an antisolvent to the solution of the step (i) to prepare a mixture.

In the preparation method of the present invention, the co-crystal of agomelatine and hydroquinone can be produced with higher yield and purity, and the process is so simple as to be applied to a mass production with ease.

The agomelatine-hydroquinone co-crystal of the present invention has a powder X-ray diffraction pattern showing peaks (±0.2°) at Bragg angles (2 theta) of 10.40°, 17.00°, 17.50°, 18.00°, 19.25°, 20.10°, 21.00°, 21.30°, 21.75°, 22.10°, 23.55°, 24.15°, and 26.20°.

Further, the agomelatine-hydroquinone co-crystal of the present invention has a single endothermic peak in the differential scanning calorimetry (DSC) curve at 97° C. when the heating rate is 10° C./min.

In the preparation method of the present invention, the method may further comprise a step of stirring the mixture of the step (ii). The stirring step may be carried out under the conditions of minimizing the evaporation of the solvent contained in the mixture. For example, the stirring may be performed while the container of the mixture is covered with a lid.

After the addition of the antisolvent, the mixture is stirred to form co-crystals. The mixture containing the co-crystals is subjected to vacuum filtration to yield co-crystals.

In the step (i) of the preparation method for agomelatine-hydroquinone co-crystal according to the present invention, the amounts of the agomelatine and hydroquinone dissolved in the organic solvent are preferably controlled so that 1 to 2 moles of hydroquinone is used per one mole of agomelatine.

In the present invention, the organic solvent may be methylacetate, ethylacetate, diethylether, methyl-tert-butylether, or a mixture thereof, preferably ethylacetate.

In the step (ii) of the preparation method for agomelatine-hydroquinone co-crystal according to the present invention, the antisolvent may be pentane, hexane, heptane, benzene, or a mixture thereof, preferably hexane.

In the present invention, the volume ratio of the organic solvent of the step (i) to the antisolvent of the step (ii) may be 1:1 to 1:3, preferably 1:2.

In the preparation method for agomelatine-hydroquinone co-crystal according to the present invention, the stirring speed may be arbitrarily determined by those skilled in the art depending on the reacting dose. The reaction temperature is preferably the room temperature such as 20 to 30° C.

The present invention also provides a pharmaceutical composition comprising an agomelatine-resorcinol or agomelatine-hydroquinone co-crystal prepared by the method of the present invention.

The pharmaceutical composition of the present invention may have the same therapeutic uses of agomelatine. For example, the pharmaceutical composition may be a composition for prevention or treatment of depression.

In the present invention, the pharmaceutical composition may further comprise carriers, adjuvants or diluents, generally used as pharmaceutically acceptable excipients, in addition to the agomelatine-resorcinol and agomelatine-hydroquinone co-crystal, so that it can be finished into a dosage form according to a general method of formulation. For example, the pharmaceutically acceptable excipients may be saline solution, sterile water, Ringer's solution, buffered saline, dextrose solution, maltodextrin solution, glycerol, ethanol, amino acid, and a mixture of at least one thereof. Under necessity, the composition may further include another additives commonly used, such as a stabilizer, an antioxidant, a buffer solution, a bacteriostat, etc.

Under necessity, the pharmaceutical composition of the present invention may be taken by an appropriate route of administration, oral or non-oral. Depending on the route of administration, the pharmaceutical composition may be formulated into an appropriate dosage form of a liquid, such as an aqueous solution, a suspension, an emulsion, etc., pills, capsules, granules, or tablets.

In the present invention, the daily effective dose of the pharmaceutical composition is 1 mg to 3,000 mg for adults. But, the dosage depends on the patient's age, weight, sex, administration route, health condition, and the severity of disease. The daily dose may be administered once or multiple times a day.

The present invention also provides a method for preventing or treating depression by administering the pharmaceutical composition comprising an agomelatine-resorcinol or agomelatine-hydroquinone co-crystal as prepared according to the method of the present invention into a mammal including a human.

The present invention also provides the use of the agomelatine-resorcinol or agomelatine-hydroquinone co-crystal as prepared according to the method of the present invention for the prevention or treatment of depression.

Advantageous Effect

The preparation method for agomelatine-resorcinol and agomelatine-hydroquinone co-crystal according to the present invention involves such a simple and easy preparation process as to enable a commercial mass production.

Relative to the conventional crystal form (polymorph type II) of agomelatine, the agomelatine-resorcinol or agomelatine-hydroquinone co-crystal of the present invention displays high dissolution rate in both acidic and neutral media and high stability to maximize the therapeutic effects of agomelatine.

MODE FOR INVENTION

Hereinafter, the disclosure of the present invention will be described in further detail with reference to examples, which are given for the understanding of the disclosure of the present invention and not intended to limit the scope of the claims in the present invention. The examples of the present invention are provided for those skilled in the related art of the present invention to completely understand the present invention.

<Example 1> Preparation Method for Agomelatine-Resorcinol Co-Crystal Using Ethylacetate and Hexane as a Solvent and an Antisolvent, Respectively 1.825 g of agomelatine (polymorph type II, ≥99.85%, Changzhou Ruiming Pharmaceutical Co., Changzhou, China) and 0.826 g of resorcinol (≥99%, Sigma Aldrich, St. Louis, Mo.) were accurately weighed and put into a 100 mL glass bottle. 15 mL of ethylacetate was added, and the glass bottle was covered with a lid and then kept under stirring at the room temperature for 5 minutes to dissolve agomelatine and resorcinol. 30 ml of hexane was added to the resultant clear ethylacetate solution in which agomelatine and resorcinol were completely dissolved. The glass bottle was covered with a lid and then kept under stirring for another 30 minutes to cause formation of solid crystals. The solid thus obtained was collected through vacuum filtration and then vacuum-dried for 24 hours to obtain a solid compound, which was kept at the room temperature.

<Example 2> Preparation Method for Agomelatine-Hydroquinone Co-Crystal Using Ethylacetate and Hexane as a Solvent and an Antisolvent, Respectively 1.825 g of agomelatine (polymorph type II, ≥99.85%, Changzhou Ruiming Pharmaceutical Co., Changzhou, China) and 0.826 g of hydroquinone (≥99%, Sigma Aldrich, St. Louis, Mo.) were accurately weighed and put into a 100 mL glass bottle. 15 mL of ethylacetate was added, and the glass bottle was covered with a lid and then kept under stirring at the room temperature for 5 minutes to dissolve agomelatine and hydroquinone. 30 ml of hexane was added to the resultant clear ethylacetate solution in which agomelatine and hydroquinone were completely dissolved. The glass bottle was covered with a lid and then kept under stirring for another one hour to cause formation of solid crystals. The solid thus obtained was collected through vacuum filtration and then vacuum-dried for 24 hours to obtain a solid compound, which was kept at the room temperature.

<Preparation Example 1> Preparation Method for Agomelatine-Resorcinol Co-Crystal Using Ball-Mill Process An agomelatine-resorcinol co-crystal was prepared according to the ball-mill method as specified in the KR 1404836. 1.22 g of agomelatine (polymorph type II, ≥99.85%, Changzhou Ruiming Pharmaceutical Co., Changzhou, China) and 0.552 g of hydroquinone (≥99%, Sigma Aldrich, St. Louis, Mo.) were accurately weighed and put into a 250 mL zirconia milling pot. Filled with zirconia balls, the zirconia milling pot was sealed tight, placed on rollers and then subjected to milling at 350 rpm. After 48-hour milling, the powder was collected from the pot to obtain an agomelatine-hydroquinone co-crystal.

<Preparation Example 2> Preparation Method for Agomelatine-Resorcinol Co-Crystal Using Evaporation Process An agomelatine-resorcinol co-crystal was prepared according to the evaporation method as specified in the KR 1404836. 1.22 g of agomelatine (polymorph type II, ≥99.85%, Changzhou Ruiming Pharmaceutical Co., Changzhou, China) and 0.552 g of hydroquinone (≥99%, Sigma Aldrich, St. Louis, Mo.) were accurately weighed and put into a 250 mL beaker. 100 ml of ethylacetate was added, and the beaker was covered with a lid and kept under stirring at the room temperature for 30 minutes to dissolve agomelatine and hydroquinone completely. After the complete dissolution of agomelatine and hydroquinone, the lid was removed from the beaker, allowing the ethylacetate to evaporate. In 20 hours, the solid was collected from the beaker in which the ethylacetate dried out. Using a vacuum pump, the solid thus obtained was vacuum-dried to yield the agomelatine-hydroquinone co-crystal of the present invention.

<Experimental Example 1> X-Ray Diffraction (XRD) Analysis

An X-ray diffraction (XRD) analysis was performed on the agomelatine-resorcinol co-crystal of Example 1, the agomelatine-hydroquinone co-crystal of Example 2, the agomelatine crystal, and the resorcinol and hydroquinone crystals.

The powder XRD diffraction patterns were obtained with Rigaku DMAX-2200 XRD analysis equipment using 0.154 nm Cu-Kα as a solid state detector under the conditions of 40 kV/40 mA.

200 mg of each powder specimen was chopped on a silica mount to have flat surface, and the Bragg angles (2 theta) in the range of 5 to 35 degrees (°) were measured with the step size of 0.05° and the goniometer rate of 3 seconds per step.

Figure 1:
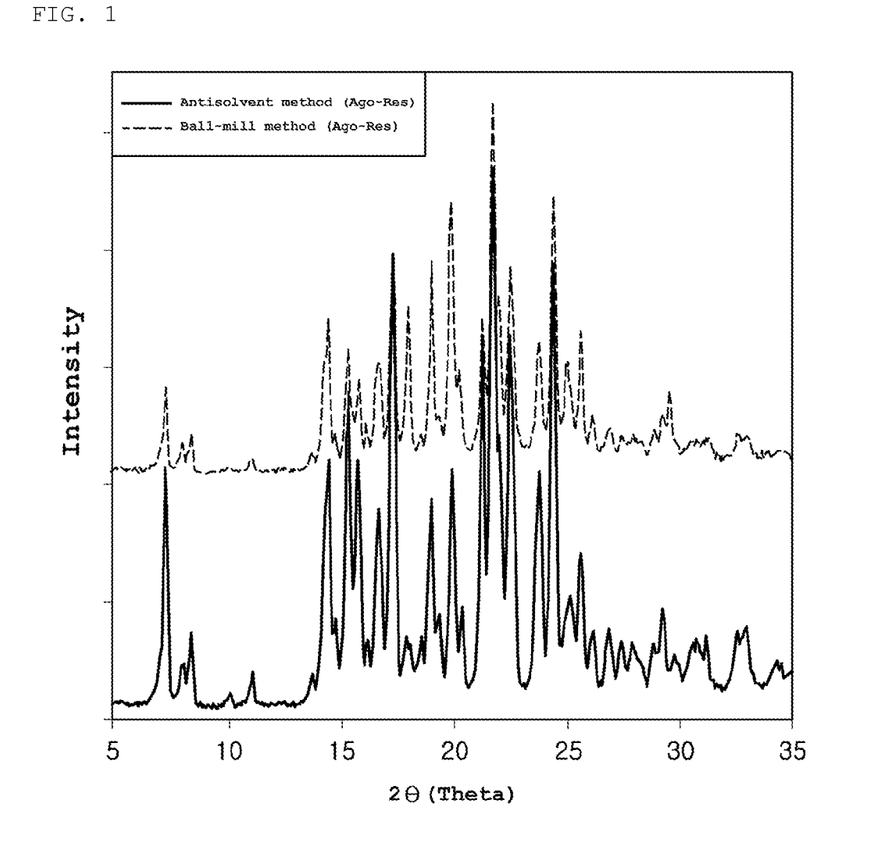
FIGS. 1 to 3 are diagrams showing the powder XRD diffraction patterns of the agomelatine-resorcinol co-crystal of the present invention (solid line), a conventional agomelatine crystal form (polymorph type II, ≥99.85%, Changzhou Ruiming Pharmaceutical Co., Changzhou, China) and a resorcinol crystal form (≥99.85%, Sigma Aldrich, St. Louis, Mo.), respectively, where the horizontal axis represents 2 theta (Bragg angle, °); and the vertical axis represents the intensity (cps).

The XRD analysis results of the agomelatine-resorcinol co-crystal obtained in Example 1 are presented in FIG. 1 and Table 1.

The XRD pattern analysis results of the agomelatine crystal form (polymorph type II, ≥99.85%, Changzhou Ruiming Pharmaceutical Co., Changzhou, China) and the resorcinol crystal form (≥99%, Sigma Aldrich, St. Louis, Mo.) are presented in FIGS. 2 and 3, respectively.

TABLE 1

| 2θ (±0.2°) | Intensity | I (%) | 2θ (±0.2°) | Intensity | I (%) |
|---|---|---|---|---|---|
| 7.25 | 2149 | 43.19 | 19.95 | 2116 | 42.52 |
| 7.95 | 461 | 9.26 | 20.40 | 956 | 19.21 |
| 8.35 | 735 | 14.79 | 21.30 | 3327 | 66.86 |
| 11.05 | 400 | 8.04 | 21.75 | 4976 | 100.00 |
| 14.30 | 1837 | 36.92 | 22.05 | 2412 | 48.47 |
| 14.45 | 2212 | 44.45 | 22.50 | 3268 | 65.67 |
| 14.75 | 858 | 17.24 | 23.75 | 2091 | 42.02 |
| 15.35 | 2778 | 55.82 | 24.40 | 3921 | 78.80 |
| 15.75 | 2197 | 44.15 | 25.15 | 1046 | 21.02 |
| 16.10 | 647 | 13.00 | 25.60 | 1402 | 28.18 |
| 16.70 | 1786 | 35.89 | 26.15 | 747 | 15.01 |
| 17.35 | 3950 | 79.38 | 26.90 | 751 | 15.09 |

TABLE 1-continued

| 2θ (±0.2°) | Intensity | I (%) | 2θ (±0.2°) | Intensity | I (%) |
|---|---|---|---|---|---|
| 17.95 | 701 | 14.09 | 29.25 | 936 | 18.81 |
| 18.60 | 699 | 14.05 | 29.80 | 549 | 11.03 |
| 19.05 | 1866 | 37.50 | 32.60 | 742 | 14.91 |
| 19.35 | 901 | 18.11 | 33.00 | 782 | 15.71 |

Figure 2:
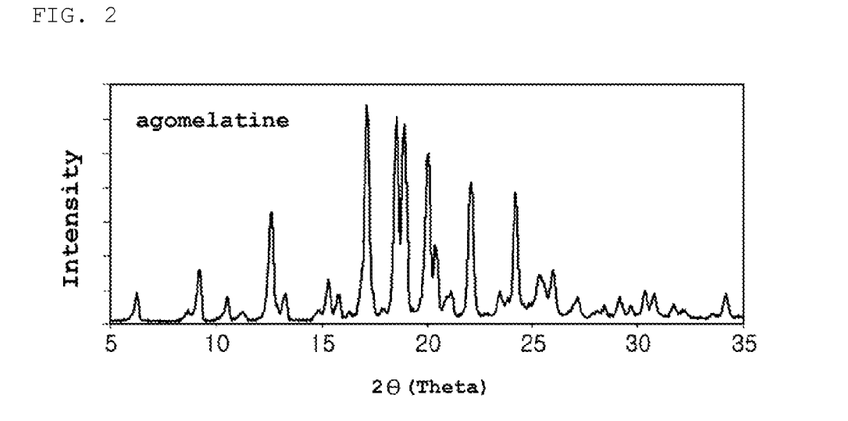
Figure 3:
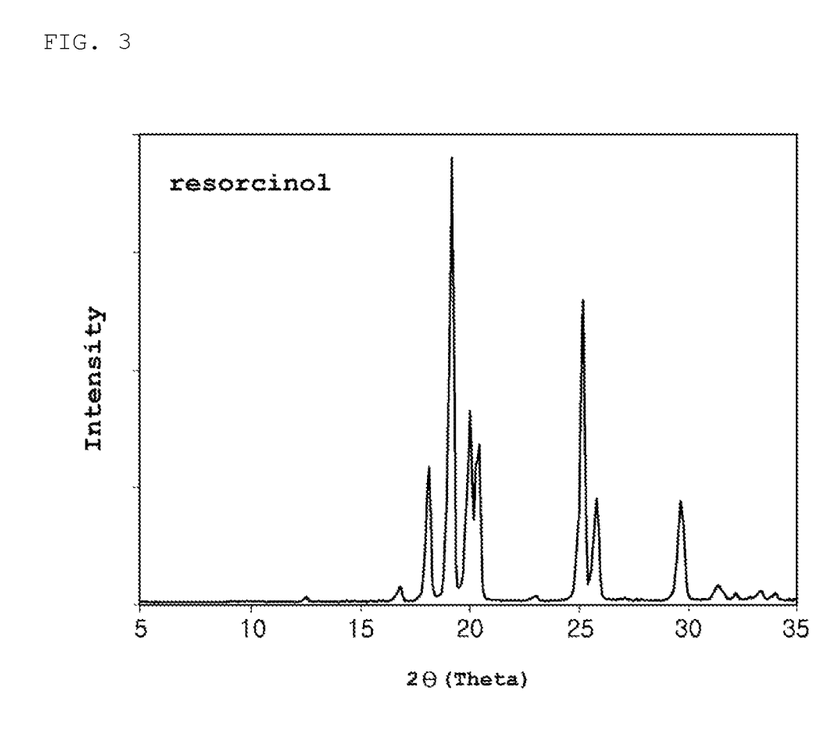

As can be seen from FIGS. 1 to 3 and Table 1, the agomelatine-resorcinol co-crystal (solid line) synthesized in Example 1 has a unique diffraction pattern as different from the agomelatine crystal form and the resorcinol crystal form. This explicitly shows that the agomelatine-resorcinol co-crystal is synthetically prepared.

FIG. 1 presents a comparison of the X-ray diffraction pattern between the co-crystal prepared by the conventional ball-mill method in Preparation Example 1 and the co-crystal synthesized in Example 1. Overall, the co-crystal synthesized in Example 1 has the larger peaks. This reveals that the agomelatine-resorcinol co-crystal synthesized in Example 1 displays the enhanced crystallinity relative to the co-crystal prepared by the conventional ball-mill method. That is, the antisolvent method of the present invention rather than the ball-mill method leads to a preparation of agomelatine-resorcinol co-crystals with higher crystallinity.

The same procedures of the XRD pattern analysis were performed for the agomelatine-hydroquinone co-crystal of Example and the hydroquinone crystal form. The analysis results are presented in FIGS. 7 and 8 and Table 2. As can be seen from FIGS. 7 and 8 and Table 2, the agomelatine-hydroquinone co-crystal has a unique diffraction pattern as different from the agomelatine crystal form and the hydroquinone crystal form. This explicitly shows that the agomelatine-hydroquinone co-crystal is synthetically prepared.

TABLE 2

| 2θ (±0.2°) | Intensity | I (%) |
|---|---|---|
| 10.40 | 6307 | 97.20 |
| 12.35 | 347 | 5.35 |
| 13.40 | 673 | 10.37 |
| 15.00 | 909 | 14.01 |
| 15.25 | 970 | 14.95 |
| 16.15 | 672 | 10.36 |
| 17.00 | 2113 | 32.56 |
| 17.50 | 1299 | 20.02 |
| 18.00 | 4636 | 71.44 |
| 18.60 | 696 | 10.73 |
| 19.25 | 1436 | 22.13 |
| 20.10 | 3722 | 57.36 |
| 21.00 | 6489 | 100.00 |
| 21.30 | 1780 | 27.43 |
| 21.75 | 1522 | 23.46 |
| 22.10 | 4685 | 72.20 |
| 22.60 | 887 | 13.67 |
| 23.55 | 1725 | 26.58 |
| 24.15 | 5270 | 81.21 |
| 25.15 | 791 | 12.19 |
| 25.70 | 844 | 13.01 |
| 26.20 | 2960 | 45.62 |
| 26.80 | 494 | 7.61 |
| 27.20 | 974 | 15.01 |
| 28.15 | 265 | 4.08 |
| 28.65 | 468 | 7.21 |
| 29.15 | 1260 | 19.42 |
| 29.30 | 1154 | 17.78 |
| 30.50 | 567 | 8.74 |
| 31.05 | 523 | 8.06 |
| 31.70 | 915 | 14.10 |
| 33.95 | 646 | 9.96 |

Figure 7:
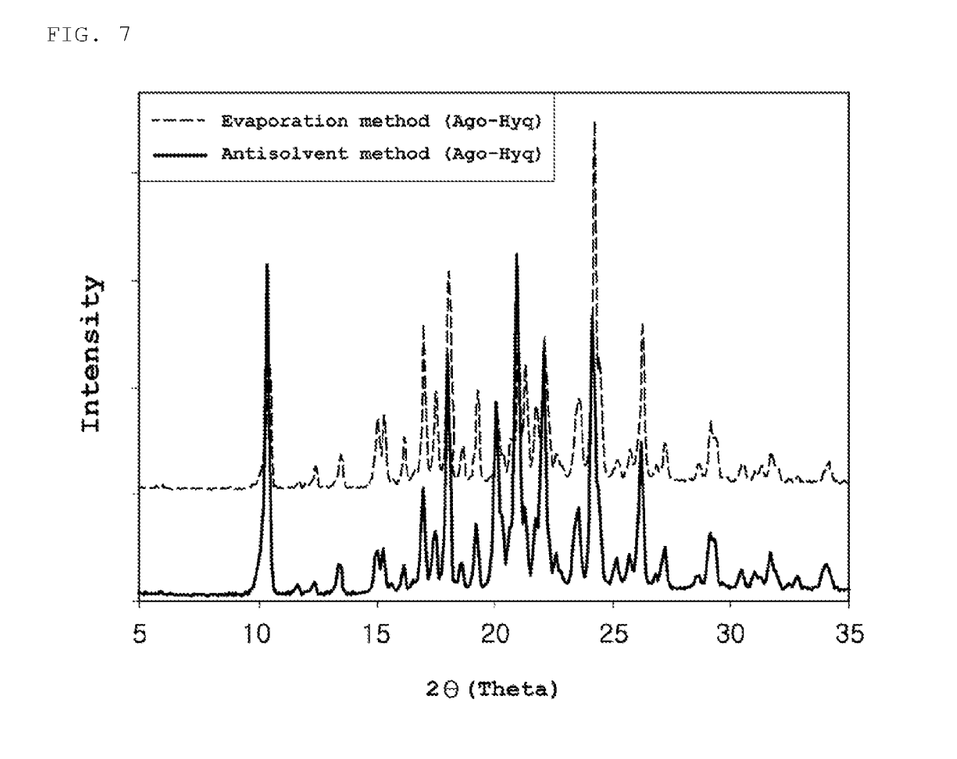
FIGS. 7 and 8 are diagrams showing the powder XRD diffraction patterns of the agomelatine-hydroquinone co-crystal of the present invention and a hydroquinone crystal form (≥99%, Sigma Aldrich, St. Louis, Mo.), respectively, where the horizontal axis represents 2 theta (Bragg angle, °); and the vertical axis represents the intensity (cps).
Figure 8:
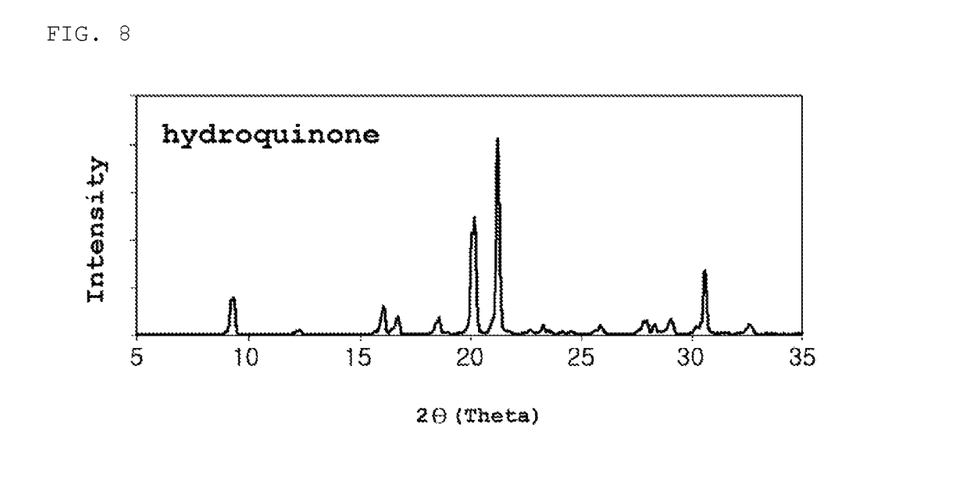

As can be seen form FIG. 7, from a comparison of the X-ray diffraction pattern between the co-crystal of Preparation Example 2 prepared by the conventional evaporation method and the co-crystal synthesized in Example 2, the co-crystal of Example 2 has a little bit larger peaks. This explicitly shows that the synthesized agomelatine-hydroquinone of Example 2 has a slightly higher crystallinity. That is, the antisolvent method of the present invention rather than the evaporation method results in preparing agomelatine-hydroquinone co-crystals with higher crystallinity.

<Experimental Example 2> Differentiation Scanning Calorimetry (DSC) Analysis

The agomelatine-resorcinol co-crystal of Example 1, the agomelatine crystal form and the resorcinol crystal form were measured in regards to the endothermic properties using DSC-60 (Shimadzu, Japan) analysis equipment.

5 mg of each powder specimen was placed in an aluminum container. Using an empty aluminum container as a reference, the DSC value was measured. The DSC measurement was performed in the nitrogen atmosphere at temperature ranging from 30° C. to 300° C. and a heating rate of 10° C./min.

Figure 4:
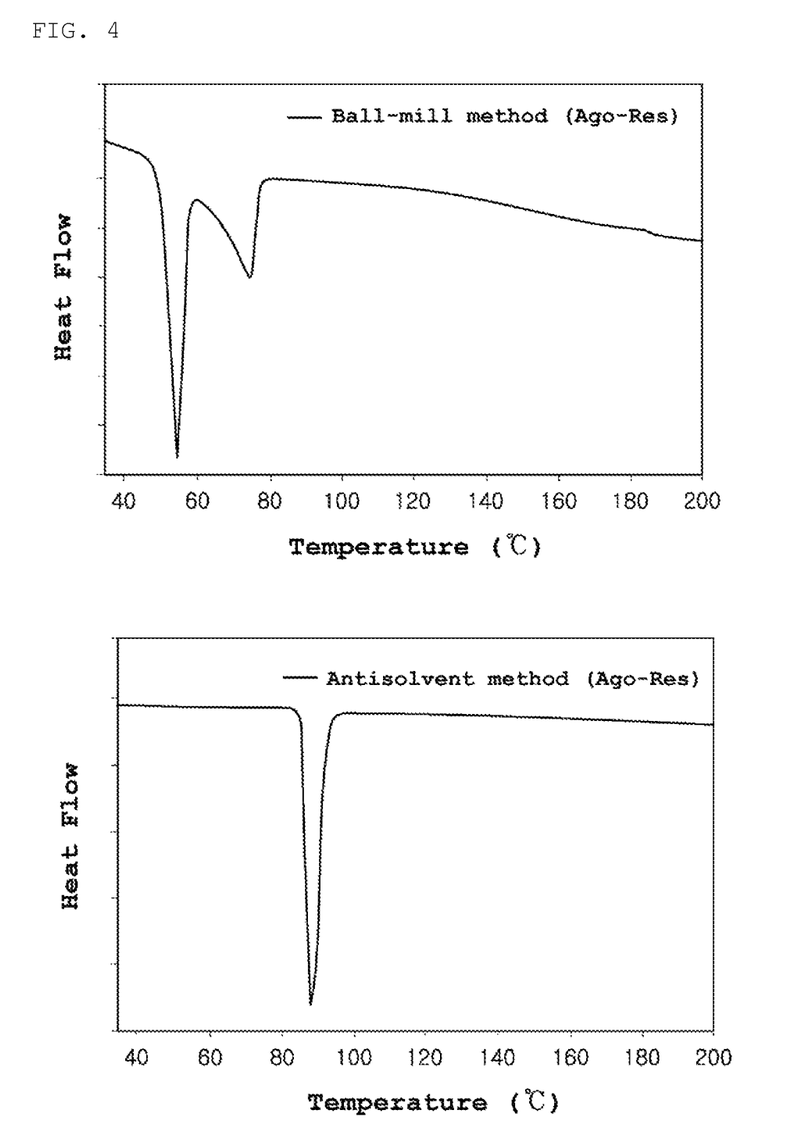
FIGS. 4 to 6 are diagrams showing the endothermic peaks in the differential scanning calorimetry (DSC) curves for the agomelatine-resorcinol co-crystal of the present invention, a conventional agomelatine crystal form (polymorph type II) and a resorcinol crystal form, respectively, where the horizontal axis represents the temperature (° C.); and the vertical axis represents the heat flow (mW).
Figure 5:
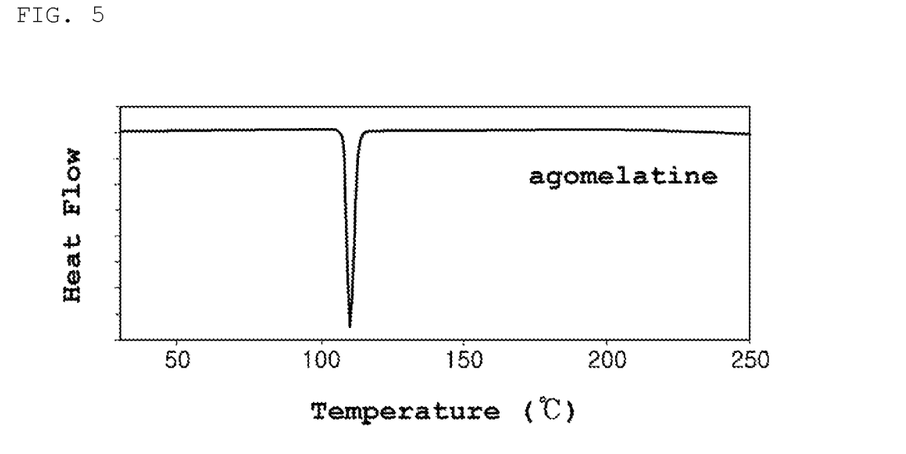
Figure 6:
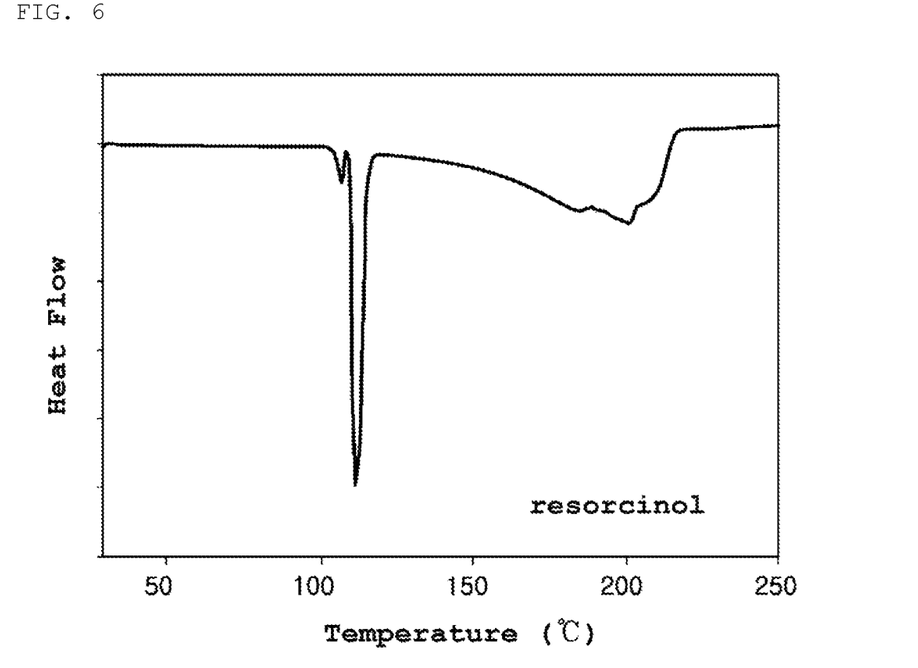

The DSC measurement results are presented in FIG. 4 for the agomelatine-resorcinol co-crystal of Example 1 and in FIGS. 5 and 6 for the agomelatine crystal form and the resorcinol crystal form, respectively.

As can be seen from the DSC measurement results, the agomelatine-resorcinol co-crystal of Example 1 according to the present invention displays a single endothermic peak at around 88° C., and the agomelatine crystal form and the resorcinol crystal form show an endothermic peak at 108° C. and 107° C., respectively. It is thus shown from FIG. 4 that the agomelatine-resorcinol co-crystal containing neither agomelatine nor resorcinol is formed. Referring to FIG. 4, the co-crystal of Preparation Example 1 using the conventional ball-mill method shows two endothermic peaks, whereas the synthesized co-crystal of Example 1 displays a single endothermic peak, which explicitly means the formation of a pure co-crystal unlike the co-crystal prepared by the ball-mill method. That is, the antisolvent method of the present invention can produce an agomelatine-resorcinol co-crystal with higher purity.

Figure 9:
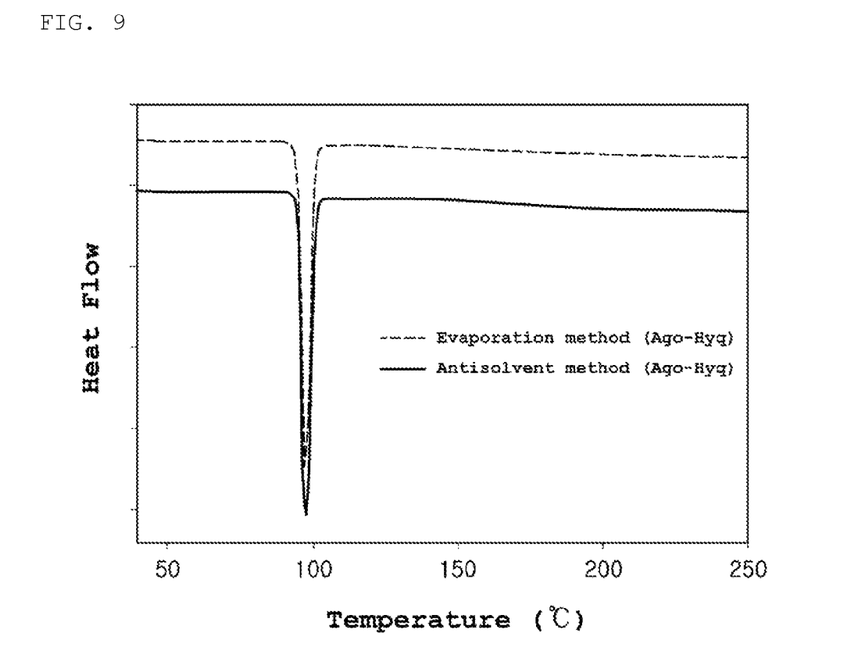
FIGS. 9 and 10 are diagrams showing the endothermic peaks in the differential scanning calorimetry (DSC) curves for the agomelatine-hydroquinone co-crystal of the present invention and a hydroquinone crystal form, respectively, where the horizontal axis represents the temperature (° C.); and the vertical axis represents the heat flow (mW).
Figure 10:
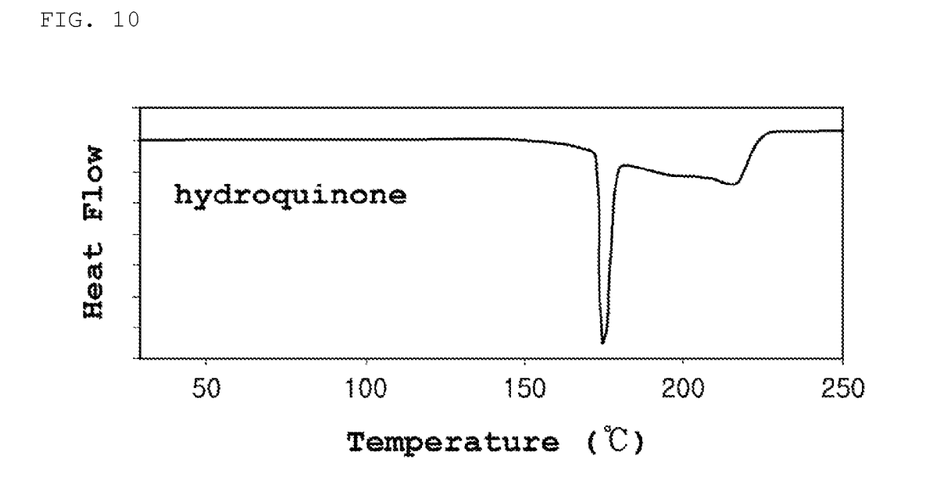

The same procedures were performed to analyze the endothermic properties of the agomelatine-hydroquinone co-crystals of Preparation Example 2 and Example 2 and the hydroquinone crystal form. The analysis results are presented in FIGS. 9 and 10. As can be seen from FIGS. 9 and 10, the agomelatine crystal form (FIG. 5) and the hydroquinone crystal form (FIG. 10) show endothermic peaks at around 108° C. and 175° C., respectively; whereas the agomelatine-hydroquinone co-crystal displays a single endothermic peak at around 97° C., which explicitly shows the formation of a pure agomelatine-hydroquinone co-crystal different from the agomelatine crystal form or the hydroquinone crystal form.

<Experimental Example 3> Comparison of Dissolution Rate

In order to measure the intrinsic dissolution rate (IDR) of agomelatine and the agomelatine-resorcinol co-crystal, 50 mg of agomelatine and 72.63 mg of the agomelatine-resorcinol co-crystal of Example 1 were molded into a number of pellets having a constant surface area and then subjected to a dissolution testing.

Each powder specimen was put in a 13 mm pellet die (Specac, UK), squeezed down under a weight of 0.5 ton for 2 minutes with a hydraulic compressor and then molded into pellets having a constant surface area of 1.33 $cm^2$.

The pellets thus obtained were immobilized in 900 ml of a testing solution (pH 1.2 HCl aqueous solution and pH 6.8 phosphate-buffer solution) at 37° C., which solution was stirred with USP equipment 2 (paddle method) operated at 50 rpm. Then, the concentration of the agomelatine released from the pellets was measured.

3 ml of the testing solution was collected each time of 3 min, 5 min, 10 min, 15 min, 20 min, 25 min, 30 min, 45 min, 60 min, 75 min, 90 min, 105 min, and 120 min. The concentration (dissolved amount) of agomelatine in the collected solution was measured with UV-3600 (Shimadzu, Japan) spectrochemical analysis equipment.

Figure 11:
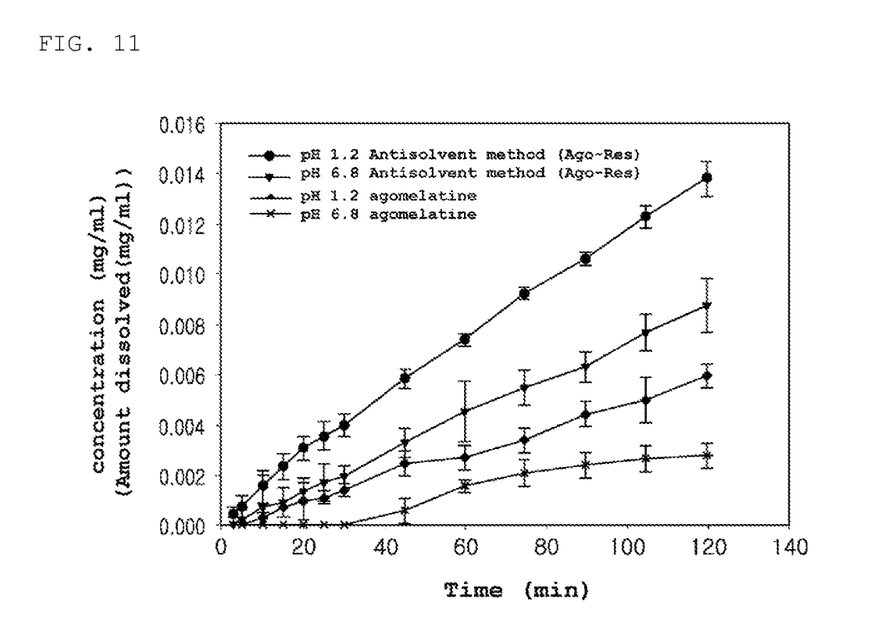
FIG. 11 is a diagram showing the dissolution rate of the agomelatine-resorcinol co-crystal of the present invention and a conventional agomelatine crystal form (polymorph type II) in acidic and neutral media, respectively, where the horizontal axis represents the time (min); and the vertical axis represents the concentration (mg/ml).

FIG. 11 presents the results of the dissolution testing for the agomelatine and the agomelatine-resorcinol co-crystal in an aqueous solution of HCl (pH 1.2) and a phosphate-buffered solution (pH 6.8). From the analysis results, the intrinsic dissolution rate (IDR) was determined and presented in Table 3 in terms of ratio.

TABLE 3

| Medium | Test substance | Dissolution rate |
|---|---|---|
| pH = 1.2 | Agomelatine | 1.0 |
| | Agomelatine-resorcinol co-crystal (1:1) | 2.3 |
| pH = 6.8 | Agomelatine | 1.0 |
| | Agomelatine-resorcinol co-crystal (1:1) | 3.2 |

As apparent from the table, the agomelatine-resorcinol co-crystal prepared in the present invention displays dissolution rate 2.3-fold higher in the acidic medium and 3.2-fold higher in the neutral medium than agomelatine. This shows that the agomelatine-resorcinol co-crystal prepared in the present invention has the higher dissolution rate, promising remarkably great therapeutic effects.

<Experimental Example 4> Thermal Stability Testing

The agomelatine-resorcinol co-crystal powder obtained in Example 1 was kept at 70° C. for 30 days and then subjected to X-ray diffraction analysis. The analysis results are presented in FIG. 12.

Figure 12:
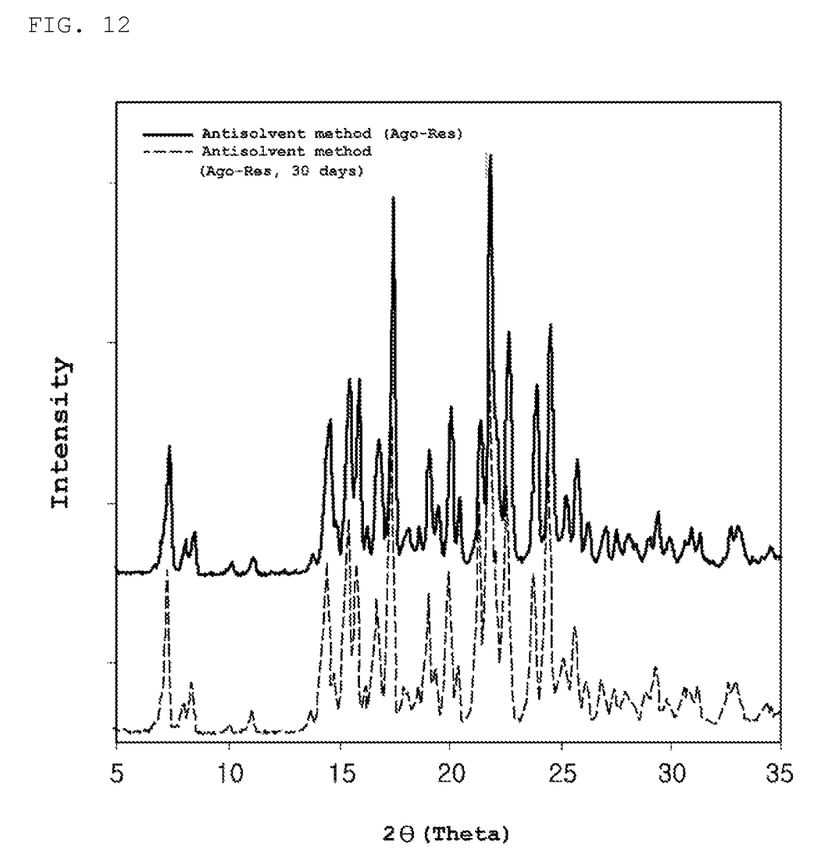
FIG. 12 is a diagram showing the thermal stability of the agomelatine-resorcinol co-crystal of the present invention, where the horizontal axis represents 2 theta (Bragg angle, °); and the vertical axis represents the intensity (cps).

As can be seen from the experimental results, the collected solid specimen was exactly identical to the crystal form of the agomelatine-resorcinol co-crystal obtained in Example 1, which shows that the pure crystal form was maintained. Contrarily, deformation occurred in the agomelatine-resorcinol co-crystal of Preparation Example 1 using the conventional ball-mill method in 7 days of the same temperature conditions. This means that the synthesized agomelatine-resorcinol co-crystal of Example 1 displays higher stability than the co-crystal prepared by the conventional ball-mill method. In other words, the antisolvent method of the present invention makes it possible to produce an agomelatine-resorcinol co-crystal with higher stability.

The invention claimed is:
1. A method for preparing agomelatine-resorcinol or agomelatine-hydroquinone co-crystals, the method comprising:
   (i) dissolving agomelatine and one aromatic polyhydric alcohol selected from hydroquinone and resorcinol in an organic solvent selected from the group consisting of C3-C7 ester, C2-C7 ether and a mixture thereof to prepare a solution; and (ii) adding a solvent selected from the group consisting of C5-C7 alkane, benzene and a mixture thereof as an antisolvent to the solution of the step (i) to prepare a mixture.

2. The method of claim 1, wherein the agomelatine-resorcinol co-crystal has a powder X-ray diffraction pattern showing peaks (±0.2°) at Bragg angles (2 theta) of 7.25°, 7.95°, 8.35°, 14.45°, 16.70°, 17.35°, 17.95°, 19.05°, 19.95°, 21.30°, 21.75°, 22.50°, 23.75°, and 24.40°.

3. The method of claim 1, wherein the agomelatine-resorcinol co-crystal has a single endothermic peak in the differential scanning calorimetry (DSC) curve at 88° C.

4. The method of claim 1, wherein the agomelatine-hydroquinone co-crystal has a powder X-ray diffraction pattern showing peaks (±0.2°) at Bragg angles (2 theta) of 10.40°, 17.00°, 17.50°, 18.00°, 19.25°, 20.10°, 21.00°, 21.30°, 21.75°, 22.10°, 23.55°, 24.15°, and 26.20°.

5. The method of claim 1, wherein the agomelatine-hydroquinone co-crystal has a single endothermic peak in the differential scanning calorimetry (DSC) curve at 97° C.

6. The method of claim 1, wherein the solution comprises agomelatine and resorcinol or hydroquinone at a molar ratio of 1:1 to 1:2.

7. The method of claim 1, wherein the organic solvent is at least one selected from the group consisting of methylacetate, ethylacetate, diethylether, methyl-tert-butylether, and a mixture thereof.

8. The method of claim 1, wherein the antisolvent is at least one selected from the group consisting of pentane, hexane, heptane, benzene, and a mixture thereof.

9. The method of claim 1, further comprising:
stirring the mixture of the step (ii).

* * * * *